(12) United States Patent
You et al.

(10) Patent No.: US 11,864,841 B2
(45) Date of Patent: Jan. 9, 2024

(54) METHOD OF OPERATING A SURGICAL MICROSCOPE AND SURGICAL MICROSCOPE

(71) Applicant: Carl Zeiss Meditec AG, Jena (DE)

(72) Inventors: Fang You, Aalen (DE); David Dobbelstein, Ulm (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 457 days.

(21) Appl. No.: 16/732,218

(22) Filed: Dec. 31, 2019

(65) Prior Publication Data

US 2021/0196396 A1 Jul. 1, 2021

(51) Int. Cl.
| | | |
|---|---|---|
| A61B 34/20 | (2016.01) | |
| A61B 34/00 | (2016.01) | |
| A61B 90/25 | (2016.01) | |
| G02B 21/00 | (2006.01) | |
| A61B 90/00 | (2016.01) | |
| G02B 21/32 | (2006.01) | |

(52) U.S. Cl.
CPC .............. *A61B 34/20* (2016.02); *A61B 34/74* (2016.02); *A61B 90/25* (2016.02); *A61B 90/36* (2016.02); *G02B 21/0012* (2013.01); *G02B 21/32* (2013.01)

(58) Field of Classification Search
CPC ......... A61B 34/20; A61B 34/74; A61B 90/25; A61B 90/36; A61B 90/20; A61B 2090/502; G02B 21/0012; G02B 21/32
See application file for complete search history.

(56) References Cited

U.S. PATENT DOCUMENTS

| | | |
|---|---|---|
| 5,641,288 A | 6/1997 | Zaenglein, Jr. |
| 5,825,982 A | 10/1998 | Wright et al. |
| 6,459,926 B1 | 10/2002 | Nowlin et al. |
| 7,190,513 B2 | 3/2007 | Obrebski et al. |
| 2004/0036962 A1 | 2/2004 | Brunner et al. |
| 2006/0028400 A1 | 2/2006 | Lapstun et al. |
| 2009/0190209 A1 | 7/2009 | Nakamura |
| 2012/0307027 A1 | 12/2012 | Popovic et al. |

(Continued)

FOREIGN PATENT DOCUMENTS

| | | |
|---|---|---|
| WO | 2015151447 A1 | 10/2015 |
| WO | 2018078470 A1 | 5/2018 |

OTHER PUBLICATIONS

U.S. Appl. No. 16/732,126, filed Dec. 31, 2019, Fang You et al., Carl Zeiss Meditec AG.

(Continued)

*Primary Examiner* — Tracy Y. Li
(74) *Attorney, Agent, or Firm* — Ewers IP Law PLLC; Falk Ewers

(57) ABSTRACT

A method of operating a surgical microscope includes receiving an instruction to move the camera relative to the object, operating a zoom lens to zoom out and displaying images obtained by processing images recorded by the camera such that centers of the displayed images correspond to a target position within the recorded images and such that the magnification of the object displayed in the images is the initial magnification, wherein the target position is displaced within the recorded images relative to the first position, and operating actuators to move the camera.

14 Claims, 3 Drawing Sheets

(56) References Cited

U.S. PATENT DOCUMENTS

| | | |
|---|---|---|
| 2013/0063580 A1 | 3/2013 | Ogawa et al. |
| 2014/0049632 A1* | 2/2014 | Hemmer ............ G02B 21/0012 348/79 |
| 2014/0163359 A1 | 6/2014 | Sholev et al. |
| 2014/0275760 A1 | 9/2014 | Lee et al. |
| 2014/0303643 A1 | 10/2014 | Ha et al. |
| 2016/0170488 A1 | 6/2016 | Hanamoto |
| 2016/0225192 A1 | 8/2016 | Jones et al. |
| 2017/0059871 A1 | 3/2017 | Hashiba et al. |
| 2017/0068081 A1 | 3/2017 | Hirayama |
| 2017/0115736 A1 | 4/2017 | Patel et al. |
| 2017/0143442 A1 | 5/2017 | Tesar et al. |
| 2018/0204380 A1 | 7/2018 | Kumar et al. |
| 2018/0232050 A1 | 8/2018 | Ofek et al. |
| 2018/0338813 A1* | 11/2018 | Taguchi ............. H04N 5/23296 |
| 2018/0356880 A1 | 12/2018 | Kashihara |
| 2019/0008595 A1 | 1/2019 | Popovic et al. |
| 2019/0029765 A1 | 1/2019 | Crawford et al. |
| 2019/0294103 A1 | 9/2019 | Hauger et al. |
| 2019/0327394 A1 | 10/2019 | Ramirez Luna et al. |
| 2019/0328464 A1* | 10/2019 | Saur .......................... G06T 7/70 |
| 2019/0353457 A1 | 11/2019 | Northrup |
| 2020/0008899 A1* | 1/2020 | Tripathi ................. A61B 90/37 |
| 2021/0186624 A1 | 6/2021 | Charles |
| 2021/0196396 A1 | 7/2021 | You et al. |
| 2021/0199940 A1 | 7/2021 | You et al. |
| 2021/0349303 A1 | 11/2021 | Koch et al. |
| 2022/0035155 A1 | 2/2022 | Williams et al. |

OTHER PUBLICATIONS

U.S. Appl. No. 16/732,162, filed Dec. 31, 2019, Fang You et al., Carl Zeiss Meditec AG.

U.S. Appl. No. 16/732,195, filed Dec. 31, 2019, Fang You et al., Carl Zeiss Meditec AG.

* cited by examiner

METHOD OF OPERATING A SURGICAL MICROSCOPE AND SURGICAL MICROSCOPE

CROSS REFERENCE TO RELATED APPLICATIONS

This application relates to U.S. patent application Ser. Nos. 16/732,126, 16/732,162, and 16/732,195, filed on Dec. 31, 2019, the entire contents of which are incorporated herein by reference.

TECHNICAL FIELD

The present disclosure relates to surgical microscopes and methods of operating such surgical microscopes.

BACKGROUND

Conventional surgical microscopes include a microscope body including microscopy optics having two oculars. The microscope body is carried by a support having an articulating structure such that the microscopy optics can be positioned and repositioned relative to an object by translatory and rotatory movements. These movements are initiated by a user looking into the oculars by applying a force to the microscope body using his hands, for example. Such surgical microscopes require the user to permanently look into the oculars which is fatiguing and may create pain, for example, in the neck of the user. Moreover, the user requiring his hands for repositioning the microscope has to lay aside the currently used surgical tool to the effect that the flow of the surgery is interrupted.

Newer surgical microscopes include a camera for recording images of the object under surgery, and a display for displaying the recorded images to the user of the microscope. The user can perform the surgery assuming a convenient position of the head and watch the images on the display since looking into oculars is no longer required. Moreover, the support of these microscopes may include actuators for positioning the articulated joints of the support such that the camera is positioned with a desired orientation at a desired location in space. The desired location and orientation can be inputted into the surgical microscope by various means. For example, WO 2015/151447 A1 describes a surgical microscope in which the direction of gaze of the user and movements of the head of the user are detected to determine new positions of the camera. The actuators of the support are then operated to reposition the camera according to the detected direction of gaze and head movements.

The technologies described above offer significant advantages over the conventional surgical microscope having oculars. Still, it has been found that the process of positioning the camera could be improved.

SUMMARY

The present disclosure has been achieved by taking the above considerations into account, and it is an object of the present disclosure to provide a surgical microscope and a method of operating such surgical microscope thereby improving the user experience in operations involving a repositioning of the camera.

According to an aspect of the disclosure, a surgical microscope includes at least one camera having a zoom lens, a support for the at least one camera and having at least one actuator for positioning the at least one camera relative to an object, and a display configured to display images obtained by processing images recorded by the at least one camera.

According to an aspect of the disclosure, a method of operating the surgical microscope includes positioning the at least one camera to have an initial position relative to the object and displaying images obtained by processing the images recorded by the at least one camera such that centers of the displayed images correspond to a first position within the recorded images and such that a magnification of the object displayed in the images is a given magnification.

According to an aspect of the disclosure, the method includes receiving an instruction to move the camera relative to the object, and, upon receipt of this instruction, operating the zoom lens to zoom out and displaying the processed images such that centers of the displayed images correspond to a second position within the recorded images and such that the magnification of the object displayed in the images is the given magnification. The second position is displaced within the recorded images relative to the first position.

Further, upon receipt of the instruction, the at least one actuator can be operated to move the at least one camera to a destination position. The destination position can be determined based on information included in the instruction to move the camera, or on information obtained from other sources. Moreover, the second position within the recorded image can be determined based on information included in the instruction to move the camera, or on information obtained from other sources.

The inventors have found that the repositioning of the cameras by operating the actuators of the support of the conventional surgical microscope may take a considerable amount of time. While new destination positions of the camera can be entered by the user quickly, for example by indicating new positions by gazing at desired positions within the displayed images, the operation of the actuators is slow since the weight of the camera and the weight of at least some of the articulated joints must be moved. The user watching the images displayed on the display of the conventional surgical microscope will have to wait a considerable amount of time until the camera has reached its destination position and until the corresponding movement in the displayed images has settled.

The inventors have further found that the zoom lens allows rapid changes of the magnification of the object displayed on the display.

When the user instructs a displacement of the microscope from the initial position to the destination position, the user expects that the displayed field of view of the camera is displaced by a certain amount and that the magnification of the object does not change. According to an aspect of the disclosure, this expectation of the user is fulfilled by operating the zoom lens to zoom out until the field of the object corresponding to the field of view of the camera in the destination position comes into the field of view of the camera located at the initial position. Herein, the magnification of the object in the detected images is reduced due to the zooming out of the zoom lens. A cropping operation can then be applied to the detected images such that the field of view of the displayed images corresponds to the expected field of view in the destination position of the camera. Therefore, when the operating of the zoom lens to zoom out has completed, the user may already see images as if the at least one camera had already been moved to its destination position. Thereafter, the actuators of the support can be operated to move the camera to its destination position. During this process, the cropping of the recorded images is also performed such that the field of view of the displayed images corresponds to the field of view of the camera in the destination position. When the camera has reached its destination position, the zoom lens can be operated to zoom in. Specifically, when the zoom lens is at a given zoom position when the instruction to move is received, the zoom lens can be operated to zoom into this given zoom position when the operating of the at least one actuator to move the at least one camera to the destination position has been completed.

According to an aspect of the disclosure, the operating of the zoom lens to zoom out requires a first duration, and the operation of the zoom lens to zoom in takes longer than the first duration. Specifically, the operation of the zoom lens to zoom in can be performed during the operation of the at least one actuator to move the at least one camera.

According to another aspect of the disclosure, the camera is a stereo camera configured to record a pair of stereo images. For example, the at least one camera may include two cameras for this purpose.

According to an aspect of the disclosure, the display is configured to display stereoscopic images. According to another aspect of the disclosure, the display is a head-mounted display which can be carried by the user of the surgical microscope. According to yet another aspect of the disclosure, the display includes a screen displaying the images obtained by processing the pair of stereo images, and a pair of glasses wearable by a user and allowing the user to see the displayed images obtained by processing left images of the pairs of stereo images with the left eye and to see the displayed images obtained by processing the right images of the pairs of stereo images with the right eye.

According to an aspect of the disclosure, the surgical microscope includes a controller configured to perform the methods described above.

BRIEF DESCRIPTION OF THE DRAWINGS

The disclosure will now be described with reference to the drawings wherein.

DESCRIPTION OF EXEMPLARY EMBODIMENTS

Figure 1:
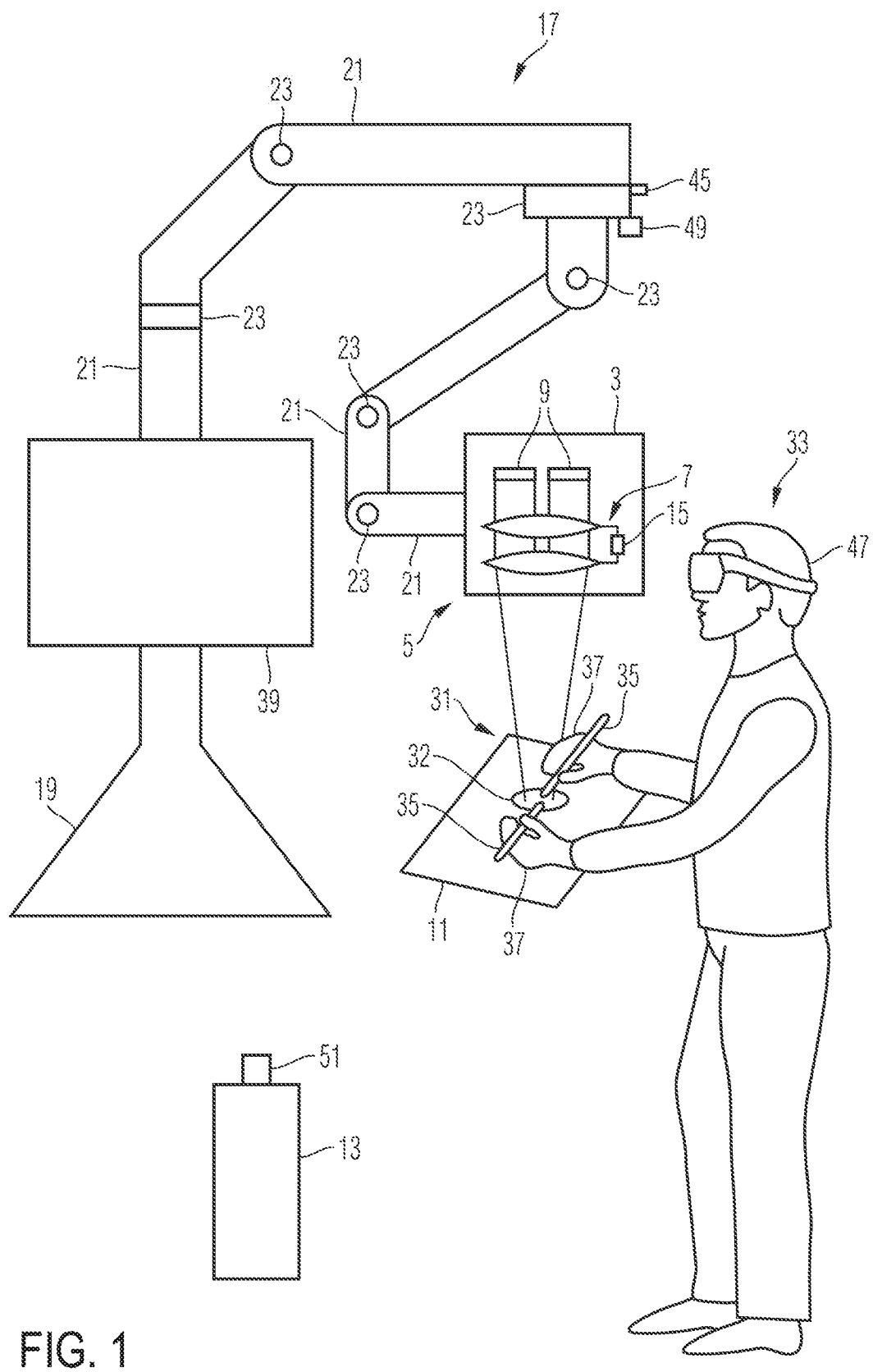
FIG. 1 is a schematic illustration of a surgical microscope.

The forgoing as well as other advantageous features of the disclosure will be more apparent from the following detailed description of exemplary embodiments with reference to the accompanying drawings. It is noted that not all possible exemplary embodiments necessarily exhibit each and every, or any, of the advantages identified herein.

In the exemplary embodiments described below, components that are alike in function and structure are designated as far as possible by alike reference numerals. Therefore, to understand the features of the individual components of a specific exemplary embodiment, the descriptions of other exemplary embodiments and of the summary of the disclosure should be referred to.

FIG. 1 shows a schematic illustration of a surgical microscope 1. The surgical microscope 1 includes a microscope body 3, a housing, microscopy optics 5 including a magnifying zoom lens 7, and two cameras 9. The cameras 9 record images of a field of view of the cameras 9 in a focal plane 11. The optics 5 is configured to adjust a distance of the focal plane 11 from the microscope body by operating an actuator (not shown in FIG. 1) controlled by a controller 13 of the surgical microscope 1. Images of the field of view of the cameras 9 recorded by the cameras 9 are transmitted to the controller 13. The magnification of an object located in the field of view in the images recorded by the cameras 9 can be adjusted by the controller by operating an actuator 15 of the zoom lens 7.

The microscope body 3 is carried by a support 17 including a base 19 placed on a floor of an operation room, and plural members 21 connected by joints including actuators 23 controlled by the controller 13 in order to position the microscope body 3 within an accessible region of the operation room. The support 17 is configured to be controlled by the controller 13 such that the microscope body 3 performs both translatory movements in three independent directions and rotatory movements about three independent axes. Specifically, the actuators 23 of the support can be operated to position the cameras 9 such that the field of view of the cameras coincides with a surgical area 31 were a user 33 of the surgical microscope 1 performs a surgery with surgical tools 35 held by his hands 37. For this purpose, the user watches the surgical area 31 by looking at a display showing images transmitted from the controller 13. The images displayed on the display can be images obtained by processing the images recorded by the cameras 9. The processing of the images may include any image processing operation, such as cropping, rotating, contrast enhancement, color correction, and direct display of the recorded images without substantial changes to the image data.

The display can be, for example a flat panel display 39 which can be mounted on the support 17, or a head-mounted display 41 carried by the user 33.

The images recorded by the two cameras 9 are pairs of stereo images showing the surgical area from different angles. The pairs of stereo images can be watched by the user using the head-mounted display 41 so that the user 33 perceives a three-dimensional impression of the surgical area. Similarly, also the flat panel display 39 can be configured to display stereo images, wherein the user 33 will wear suitable glasses selecting the displayed images transmitted to the left and right eyes of the user. For example, the flat panel display 39 may alternatingly display the images for the left and right eyes while the glasses are active shutter glasses alternatingly transmitting light to the left and right eyes of the user 33. Moreover, the flat panel display 39 may display the images for the left and right eye of the user simultaneously using different polarization states of pixels of the screen, wherein the user 33 carries corresponding polarizing glasses.

The surgical microscope 1 further includes a sensor 45 allowing the controller to determine a position and orientation of a body portion, such as a head 47 of the user 33, relative to the microscope body 3, relative to the field of view 11 of the cameras 9 or relative to some other suitable position within the operation room. The sensor 45 can be mounted at any suitable position, such as an element of the support 17, on the display, 39 and 41. Moreover, the sensor may include a plurality of sensor elements arranged at a plurality of distributed locations.

The surgical microscope 1 further includes a sensor 49 allowing the controller 13 to determine a direction of gaze of the user 33. Specifically, the controller 13 may determine a position within the images displayed on the display 39 and 41 at which the eyes of the user are directed. Also, the sensor 49 can be mounted at any suitable position, such as an element of the support 17, on the display, 39 and 41. Moreover, the sensor may include a plurality of sensor elements arranged at a plurality of distributed locations.

The surgical microscope 1 further includes a sensor 51 allowing the controller 13 to receive commands issued by the user 33. For example, the sensor 51 may include a switch operated by the user 33 to enter a start command and a stop command. Moreover, the sensor 51 may include a microphone allowing the controller 13 to detect voice commands, such as "start" and "stop".

A method of positioning the cameras relative to an object 32 within the surgical area 31 will be described with reference to FIGS. 2A to 2D and 3A and 3B below. FIGS. 2A to 2D illustrate fields of view of the cameras 9 and processed images at four different times t1, t2, t3, and t4, respectively. FIG. 3A is a time chart showing positions of the field of view of the cameras 9 in an x-direction in dependence of time, and FIG. 3B shows a magnification M of the zoom lens 7 in dependence of time.

Figure 2A:
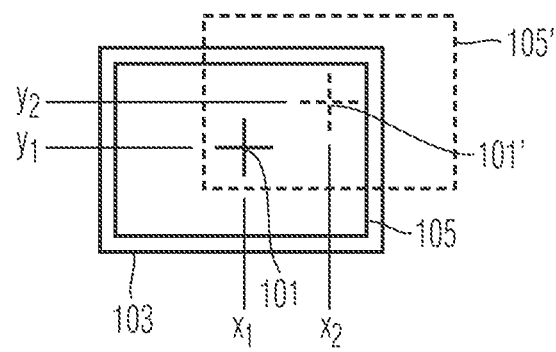
FIGS. 2A to 2D show fields of view of a camera and of processed images in a process of repositioning the cameras shown in FIG. 1, and
FIGS. 3A and 3B show graphs representing locations of the cameras and positions of the zoom lens of the cameras during the process shown in FIGS. 2A to 2D.
Figure 3A:
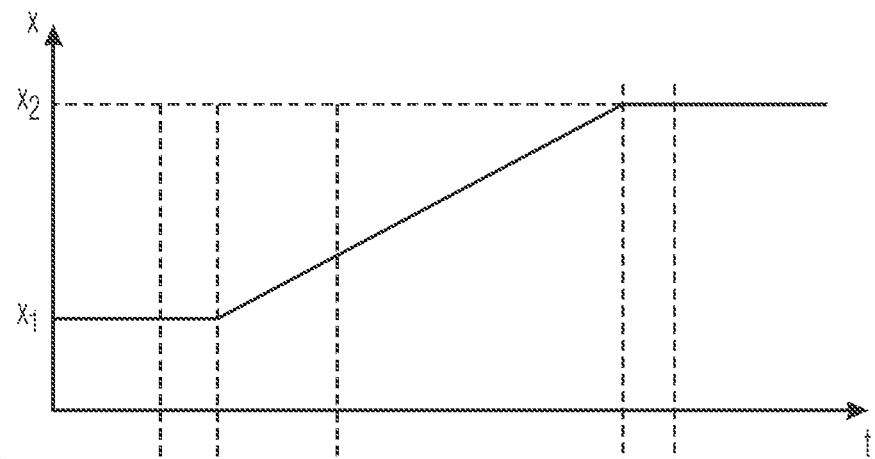
Figure 3B:
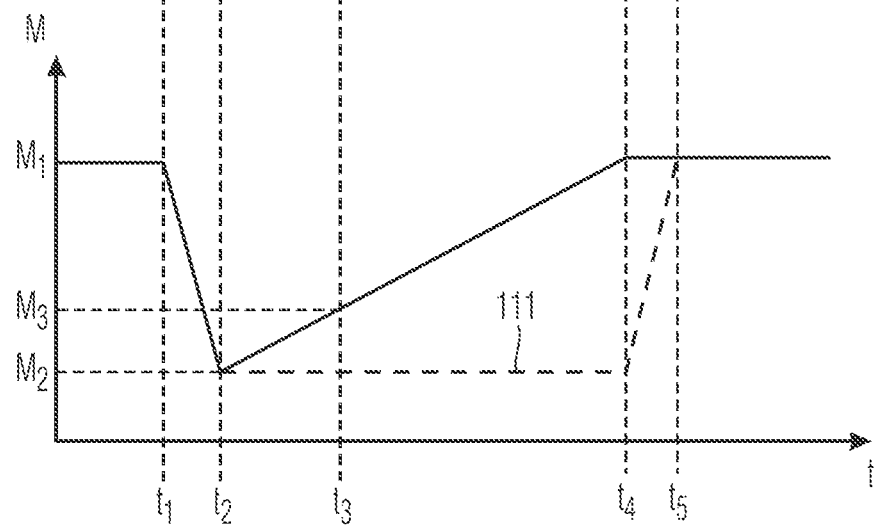

Referring now to FIG. 2A, processed images 105 displayed on the display 39 and 41 have a center 101 onto which a location (x1 and y1) of the surgical area 31 is imaged at a time t1. The center 101 is also the center of the field of view 103 of the cameras 9. The magnification of the zoom lens 7 is set to a value M1 at time t1. The field of view 103 is imaged onto the cameras 9, and the images recorded by the cameras 9 represent the field of view 103. The images recorded by the cameras 9 are processed by the controller 13 to generate the processed images 105. In the example shown in FIG. 2A, the processing of the recorded images 103 includes a cropping operation such that a small outer margin is cut away from the recorded images 103 to generate the processed images 105. This cropping operation is optional, however, and shown only for illustrative purposes to indicate the possible differences between the recorded images 103 and the processed images 105. The processed images 105 are displayed on the display 39 and 41.

The user 33 enters a command requesting a displacement of the cameras 9 at time t1. The command may include a voice command, such as the spoken word "move". This command may further include target information indicating a coordinate (x2 and y2) as the target coordinate for the center 101' of the displayed images 105' upon completion of the translatory movement of the cameras 9. This means that the controller 13 must control the actuators 23 of the support 17 such that the center 101 of the displayed images 105 is displaced from (x1 and y1) to (x2 and y2) without changing the magnification of the displayed images 105 in order to fulfill the request by the user. The center 101' and the displayed images 105' upon completion of the movement of the cameras 9 are shown in dotted lines in FIG. 2A.

Figure 2B:
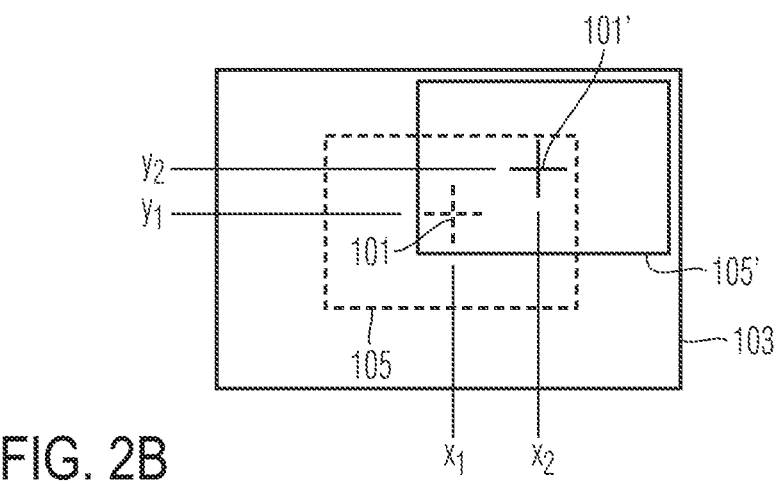

Upon receipt of the user's command, the controller 13 operates the zoom lens 7 to zoom out. This operation is completed at a time t2, where the magnification has reached the smaller value M2. The reduction of the magnification results in an increase of the field of view 103 of the cameras 9. The magnification M2 is selected such that the displayed images 105' after completion of the movement of the cameras 9 are included in the field of view 103 of the cameras 9, as shown in FIG. 2B. At that time, the recorded images corresponding to the field of view 103 are processed by a cropping operation such that the currently displayed images 105 coincide with the displayed images 105 after completion of the movement of the cameras 9. Therefore, the user may already see images displayed on the display 39 and 41 showing the operation area 31 as if the operation of moving of the cameras 9 were already completed. This is achieved already at time t2 which is only shortly after the time t1 and at which time the required movement of the cameras by operating the actuators 23 cannot be completed.

The real movement of the cameras by the actuators 23 is started at time t2 and is completed at time t4. The situation at time t4 is shown in FIG. 2D, where the displayed images 105 and the center 101 of the field of view at the time t1 are shown in dotted lines and where the displayed images 105' and the center 101' of the displayed images 105' at the time t4 are shown in full lines. The field of view 103 has the same size as the field of view 103 at time t1 which means that the magnification provided by the zoom lens 7 at time t4 is the same as the magnification provided at time t1. The cropping operation applied to the recorded images 103 cutting away a small margin is the same cropping operation performed at time t1.

Figure 2C:
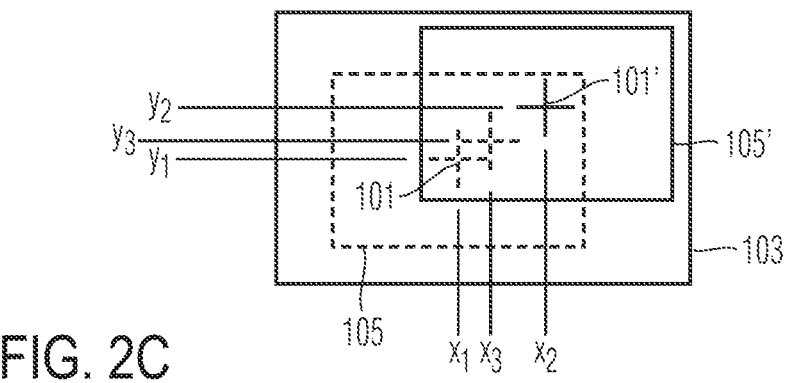
Figure 2D:
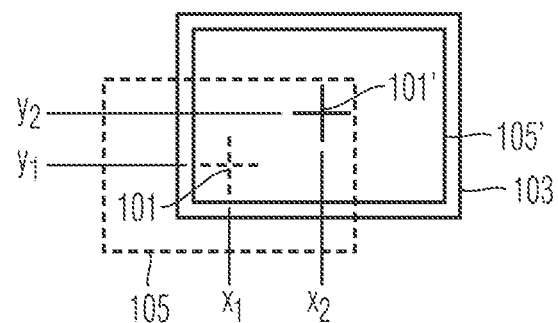

FIG. 2C shows the displayed images 105, the field of view 103 and the center 101 of the displayed images 105 in full lines at a time t3 in between times t2 and t4. At time t3, the magnification of the zoom lens 7 has a value M3 selected such that the displayed images 105' after completion of the movement of the cameras 9 are included in the field of view 103 of the cameras 9 at time t3.

The method illustrated above allows the user to see images of the operation area as if the requested displacement of the cameras 9 has already been completed after a short time (t2−t1) subsequent to the entering of the corresponding command. This time is significantly shorter than the time (t4−t2) required by the actuators 23 to complete the movement. This represents a considerable improvement of the user experience when movements of the cameras are requested. It is to be noted, however, that during the movement of the cameras, the image resolution of the displayed images is not the maximum image resolution available from the microscope. This results from the reduction of the magnification and the cropping operation applied to the displayed images during the movement of the cameras 9.

In the exemplary embodiment discussed above, the magnification is continuously increased during the movement of the cameras 9. A broken line 111 in FIG. 3B shows an alternative exemplary embodiment, in which the magnification is maintained at the value M2 while the actuators 23 are operated to displace the cameras 9. Only when this displacement is completed at time t4, the magnification is increased to the original value M1 between time t4 and time t5.

In the exemplary embodiment described above, the magnification provided at the end of the movement at time t4 is the same magnification as the initial magnification at time t1. However, according to other exemplary embodiments, the magnification can be changed together with the movement, such that the magnification provided after completion of the movement can be less than or greater than the initial magnification.

Moreover, in the exemplary embodiment described above, the target coordinate 101' is located inside the currently displayed image 105 (see FIG. 2A). However, the described method is also adapted to use target coordinates located outside the currently displayed image.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way.

Various changes may be made without departing from the spirit and scope of the present disclosure as defined in the following claims.

What is claimed is:

1. A method of operating a surgical microscope, the surgical microscope including at least one camera having a zoom lens, a support for the at least one camera, the support including at least one actuator for positioning the at least one camera relative to an object; and a display configured to display images obtained by processing the images recorded by the at least one camera, the method comprising:
   positioning the at least one camera to have an initial position relative to the object and displaying the images obtained by processing the images recorded by the at least one camera such that centers of displayed images correspond to a first position within recorded images and such that a magnification of the object displayed in the images is a given magnification;
   receiving an instruction at a first time to move the at least one camera relative to the object to a target position; and
   in response to the instruction to move the at least one camera:
   zooming out by operating the zoom lens until a field of view of the at least one camera at the target position comes into a field of view of the images recorded by the at least one camera;
   cropping the images recorded by the at least one camera such that the field of view of the displayed images corresponds to the field of view of the at least one camera at the target position;
   displaying the images obtained by processing the images recorded by the at least one camera;
   moving the at least one camera to the target position by operating the at least one actuator; and
   subsequent to zooming out, zooming in by operating the zoom lens.

2. The method of claim 1, wherein the operating of the zoom lens to zoom out takes less time to complete than the operating of the at least one actuator to move the at least one camera takes to complete.

3. The method of claim 1, wherein:
   the instruction to move the at least one camera includes target information representing the target position of the object imaged to a center of an image when the instructed operating of the at least one actuator to move the at least one camera has been completed, and
   the target position of the object is imaged to the second position within the image recorded.

4. The method of claim 1, wherein: the zoom lens is at a first zoom position at the first time, and the zoom lens is at the first zoom position after the instructed operating of the at least one actuator to move the at least one camera has been completed.

5. The method of claim 1, wherein: the operating of the zoom lens to zoom out requires a first duration, and the operation of the zoom lens to zoom in takes longer than the first duration.

6. The method of claim 1, wherein the operation of the zoom lens to zoom in is performed during the operating of the at least one actuator to move the at least one camera.

7. The method of claim 1, wherein the operating of the at least one actuator to move the at least one camera is performed such that the at least one camera performs a translatory movement.

8. The method of claim 1, wherein the operating of the at least one actuator to move the at least one camera is performed such that the at least one camera performs a rotatory movement.

9. The method of claim 1, wherein the at least one camera is a stereo camera.

10. The method of claim 9, wherein the at least one camera includes two cameras.

11. The method of claim 1, wherein the display is configured to display stereoscopic images.

12. The method of claim 11, wherein the display is a head-mounted display.

13. The method of claim 11, wherein the display comprises:
    a screen displaying the images obtained by processing the images recorded by a first camera and a second camera of the at least one camera; and
    a pair of glasses wearable by a user and allowing the user to see the displayed images obtained by processing the images recorded by the first camera with his or her left eye and to see the displayed images obtained by processing the images recorded by the second camera with his or her right eye.

14. The surgical microscope comprising:
    the at least one camera having the zoom lens;
    the support for the at least one camera and having the at least one actuator for positioning the at least one camera relative to the object;
    the display configured to display the images obtained by processing the images recorded by the at least one camera; and
    a controller configured to perform the method of claim 1 with the surgical microscope.

* * * * *